United States Patent [19]
Ochoa

[11] Patent Number: 5,888,214
[45] Date of Patent: Mar. 30, 1999

[54] PROSTHETIC LEG APPARATUS AND METHOD

[76] Inventor: Adam A. Ochoa, 4345 E. Magnolia, Phoenix, Ariz. 85034

[21] Appl. No.: 712,486

[22] Filed: Sep. 11, 1996

[51] Int. Cl.$^6$ ....................................................... A61F 2/74
[52] U.S. Cl. ................................................. 623/27; 623/35
[58] Field of Search .................................. 623/27, 32, 35, 623/38

[56] References Cited

U.S. PATENT DOCUMENTS

| | | | |
|---|---|---|---|
| 383,569 | 5/1888 | Gault | 623/35 |
| 621,638 | 3/1899 | Donaldson | 623/35 |
| 708,005 | 9/1902 | Baldwin | 623/27 |
| 2,416,817 | 3/1947 | Carter | 623/27 |
| 3,956,775 | 5/1976 | Moore | 623/27 |
| 4,089,072 | 5/1978 | Glabiszewski | 623/27 |
| 4,364,128 | 12/1982 | Mummert | 623/38 |
| 5,376,133 | 12/1994 | Gramnas | 623/38 |
| 5,445,401 | 8/1995 | Bradbury | 280/276 |
| 5,511,811 | 4/1996 | Pileggi | 280/276 |
| 5,634,652 | 6/1997 | Tsai | 280/276 |

FOREIGN PATENT DOCUMENTS 1648447  5/1991  U.S.S.R. .................................. 623/35

*Primary Examiner*—Michael J. Milano
*Attorney, Agent, or Firm*—Tod R. Nissle, P.C.

[57] ABSTRACT

A prosthetic apparatus and method facilitate the selection of a prosthetic leg having compression and expansion characteristics which are uniquely adapted to provide comfort for a particular handicapped individual. The prosthetic apparatus and method enable the compression and expansion characteristics of the apparatus to be readily adjusted without requiring the utilization of a coil spring, of compressed air, or of a hydraulic system.

4 Claims, 6 Drawing Sheets

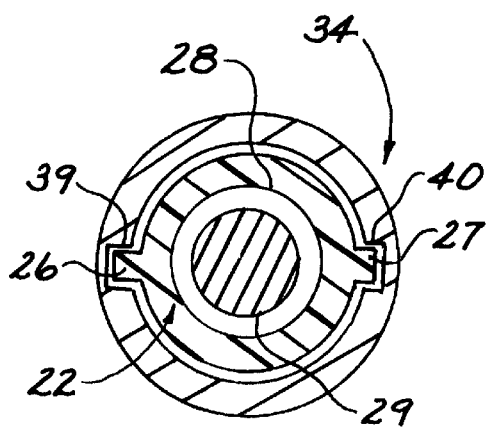
FIG. 5
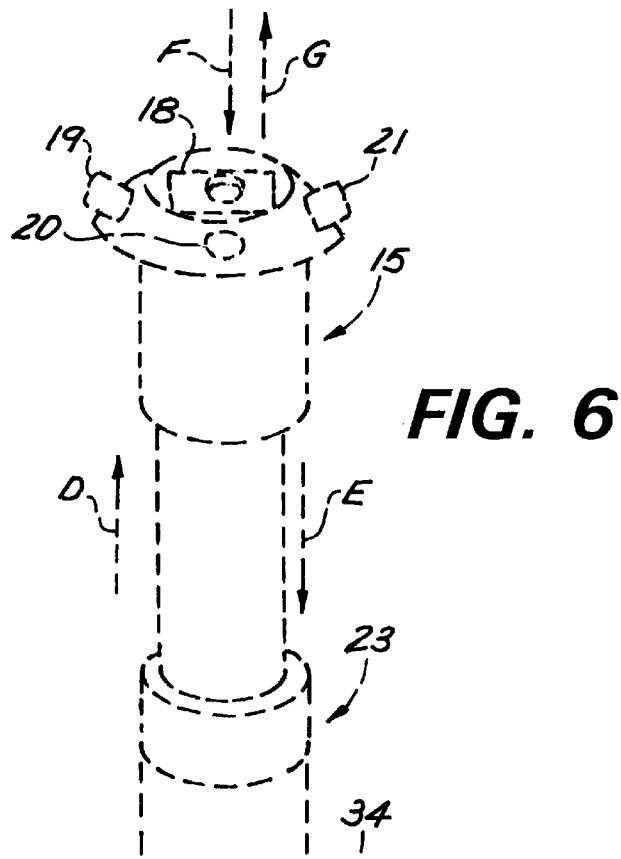
FIG. 6
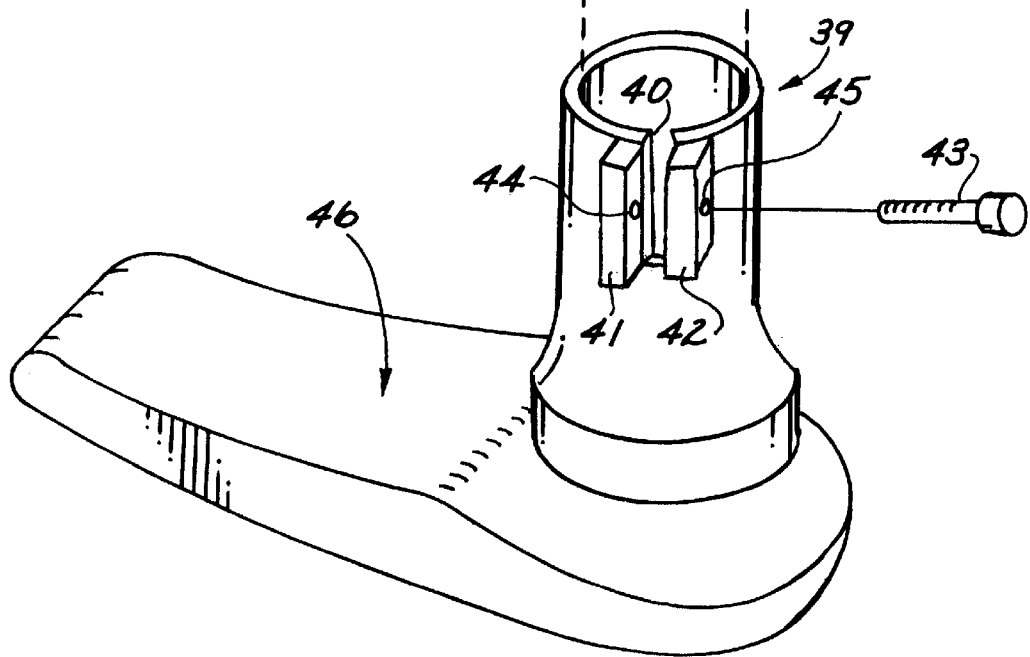

PROSTHETIC LEG APPARATUS AND METHOD

BACKGROUND OF THE INVENTION

1. Field of the Invention

This invention relates to a prosthetic apparatus and method.

More particularly, the invention relates to a prosthetic apparatus and method which facilitates the selection of a prosthetic leg having compression and expansion characteristics which are uniquely adapted to provide comfort for a particular handicapped individual.

In a further respect, the invention relates to a prosthetic apparatus and method which enables the compression and expansion characteristics of the apparatus to be readily adjusted without requiring the utilization of a coil spring, of compressed air, or of a hydraulic system.

2. Description of the Related Art Including Information Disclosed Under 37 C.F.R. Sections 1.97 to 1.99

Artificial legs are well known in the art. Such legs ordinarily are utilized by individuals who have experienced loss of part of a leg due to an accident, due to a medical procedure, or due to a wound received while serving in the military. An artificial leg is includes a cup or recess which is at the top of the artificial leg. The artificial leg is installed by placing the cup over the distal end of the "stump" or remaining portion of the user's original leg. The distal end can comprise a portion of the user's thigh or, if the amputation of the leg took place below the knee, can comprise a portion of the user's calf.

In order to soften the force of the blows which occur against the user's leg during use of the artificial leg, shock absorbers or other dampening systems are utilized in prior art artificial leg systems. Such dampening systems often appear difficult to adjust and comprise medieval looking, complicated mechanical systems which cause discomfort to the user. The cost of such systems is significant.

Accordingly, it would be highly desirable to provide an improved leg prosthesis of simple structure and manufacture which would provide an increased degree of comfort to an individual utilizing the prosthesis.

Therefore, it is a principal object of the invention to provide an improved leg prosthesis and method for installing such a prosthesis.

Another object of the invention is to provide an improved leg prosthesis which can be adapted to provide differing rates of compression and expansion.

A further object of the invention is to provide a self-lubricating compressible leg prosthesis which minimizes the play and lateral movement of slidably interacting structural members with respect to one another.

BRIEF DESCRIPTION OF THE DRAWINGS

These and other, further and more specific objects and advantages of the invention will be apparent to those skilled in the art from the following detailed description thereof, taken in conjunction with the drawings, in which:

FIG. 5 is a cross sectional view of the compression rebound unit of the invention taken along section line 5—5 thereof and illustrating additional international construction details thereof;

FIG. 6 is a perspective view illustrating the compression-rebound unit of the invention in combination with an artificial foot;

SUMMARY OF THE INVENTION

Figure 1A:
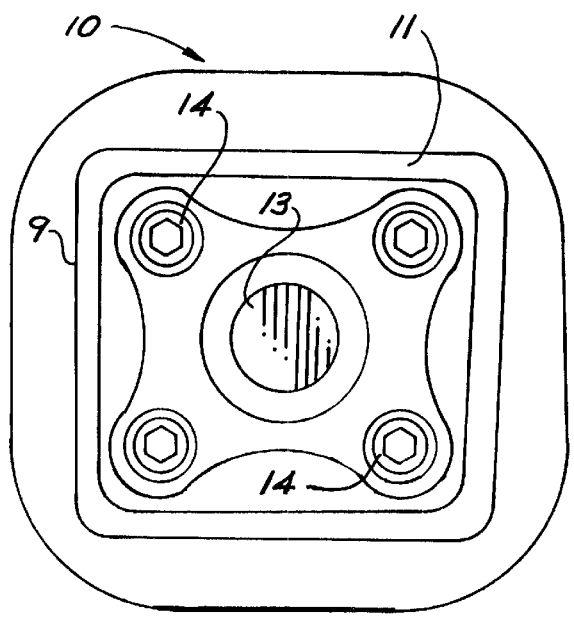
FIG. 1A is a bottom view illustrating a connection component adapted to be mounted on the distal end of the remaining portion of the leg of a handicapped individual.

Briefly, in accordance with my invention, I provide an improved prosthetic apparatus adapted for emplacement on the distal end of a leg member. The apparatus comprises a connection component adapted to be mounted on the distal end of a leg member; a foot component for contacting the ground; and, a compression-rebound unit interconnecting the connection component and the foot component. The compression-rebound unit includes a housing; a resilient elastomer mounted in the housing for compression and post-compression expansion; and, a displacement member extending into the housing. The displacement member moves in a first direction of travel and compresses the resilient elastomer when a first force is exerted against the member to press the member against and compress the elastomer; and, moves in a second direction of travel opposite the first direction of travel when the first force is released and permits the elastomer to rebound and elastically expand. The quantity of linear expansion of the elastomer per pound of force applied after the elastomer has been compressed and the force applied to the elastomer is being decreased is less than the quantity linear compression of said elastomer per pound of force applied during the compression of said elastomer.

In another embodiment of the invention, I provide an improved prosthetic apparatus adapted for emplacement on the distal end of a leg member. The apparatus comprises a connection component adapted to be mounted on the distal end of a leg member; a foot component for contacting the ground; and, a compression-rebound unit interconnecting the connection component and the foot component. The compression-rebound unit includes a housing; a resilient elastomer mounted in the housing for compression and post-compression expansion; and, a displacement member extending into the housing. The displacement member moves in a first direction of travel and compresses the resilient elastomer when a first force is exerted against the member to press the member against and compress the elastomer; and, moves in a second direction of travel opposite the first direction of travel when the first force is released and permits the elastomer to rebound and elastically expand. A key assembly is provided for sliding the displacement member in the housing along a linear axis of travel.

In a further embodiment of the invention, I provide an improved prosthetic apparatus adapted for emplacement on the distal end of a leg member. The apparatus comprises a connection component adapted to be mounted on the distal end of a leg member; a foot component for contacting the ground; and, a compression-rebound unit interconnecting the connection component and the foot component. The compression-rebound unit includes a housing; a resilient elastomer mounted in the housing for compression and post-compression expansion; and, a displacement member extending into the housing. The displacement member moves in a first direction of travel and compresses the resilient elastomer when a first force is exerted against the member to press the member against and compress the elastomer; and, moves in a second direction of travel opposite the first direction of travel when the first force is released and permits the elastomer to rebound and elastically expand.

In still another embodiment of the invention, I provide a method for emplacing a prosthesis on the distal end of a leg member. The first step of the method is providing a prosthetic apparatus. The prosthetic apparatus includes a connection component adapted to be mounted on the distal end of a leg member; a foot component for contacting the ground; and, a compression-rebound unit interconnecting the connection component and the foot component. The compression-rebound unit includes a housing; a resilient elastomer mounted in the housing for compression and post-compression expansion; and, a displacement member extending into the housing. The displacement member moves in a first direction of travel and compresses the resilient elastomer when a first force is exerted against the member to press the member against and compress the elastomer; and, moves in a second direction of travel opposite the first direction of travel when the first force is released and permits the elastomer to rebound and elastically expand. One of the elastomer units is mounted adjacent said housing. The prosthetic apparatus is mounted on the distal end of a leg member of a user. The user walks on the prosthetic apparatus to test the comfort of the apparatus. The user repeats the procedure for each of the remaining ones of the elastomer units and selects one of the elastomer units for use in the prosthetic apparatus.

DESCRIPTION OF THE PREFERRED EMBODIMENTS

Figure 1B:
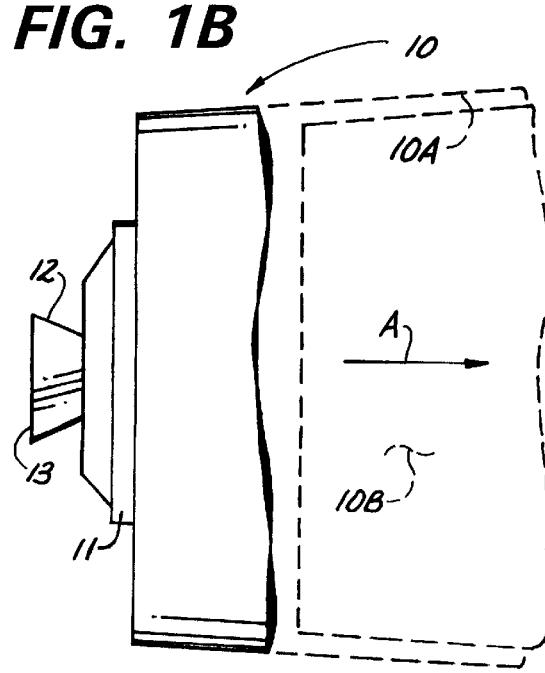
FIG. 1B is a side view further illustrating the connection component of FIG. 1A.
Figure 2:
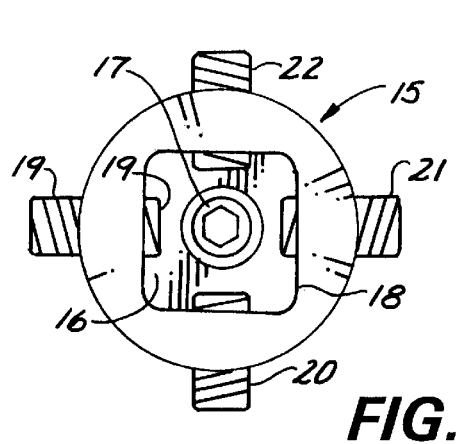
FIG. 2 is a top view illustrating a coupling member utilized in the compression-rebound unit incorporated in the leg prosthesis of the invention.

Turning now to the drawings, which depict the presently preferred embodiments of the invention for the purpose of illustrating the practice thereof and not by way of limitation of the scope of the invention and in which like reference characters refer to corresponding elements throughout the several views, FIGS. 1A and 1B illustrate a connection component 10 adapted to be mounted on the distal end of the remaining portion of the leg of a handicapped individual. If, for example, an individual has had the lower portion of his leg amputated to about mid-thigh, then component 10 fits over and receives the distal end or "stump" of the remaining length of the thigh of the leg. Straps or any other desired means can be utilized to mount removably or permanently component 10 on the remaining portion of the leg of an individual. Component 10 includes a base 9 having a wall 10A extending around a recess 10B which is shaped and dimensioned to receive the distal end of the remaining portion of an individual's leg. Plate 11 is secured to base 9 with a plurality of externally threaded hex bolts 14 which are each turned through an opening in plate 11 into base 9. Head 13 outwardly depends from plate 11 and includes four sides 12 which each taper or cant inwardly toward plate 11. As indicated in FIG. 4, head 13 is inserted in opening 18 of coupling member 15 and is secured therein by turning each of set screws 19 to 22 against a side 12.

Coupling member 15 also includes set screw 17, floor 16 and four internally threaded apertures each of which receives one of screws 19 to 22.

Figure 3:
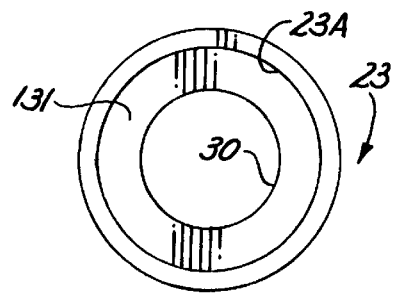
FIG. 3 is a bottom view of an internally threaded cylindrical cap utilized in the compression-rebound unit incorporated in the leg prosthesis of the invention.

The inner wall 23A of cap 23 is internally threaded. As illustrated in FIG. 3, a circular aperture 30 is formed through the top 31 of cap 30.

Figure 4:
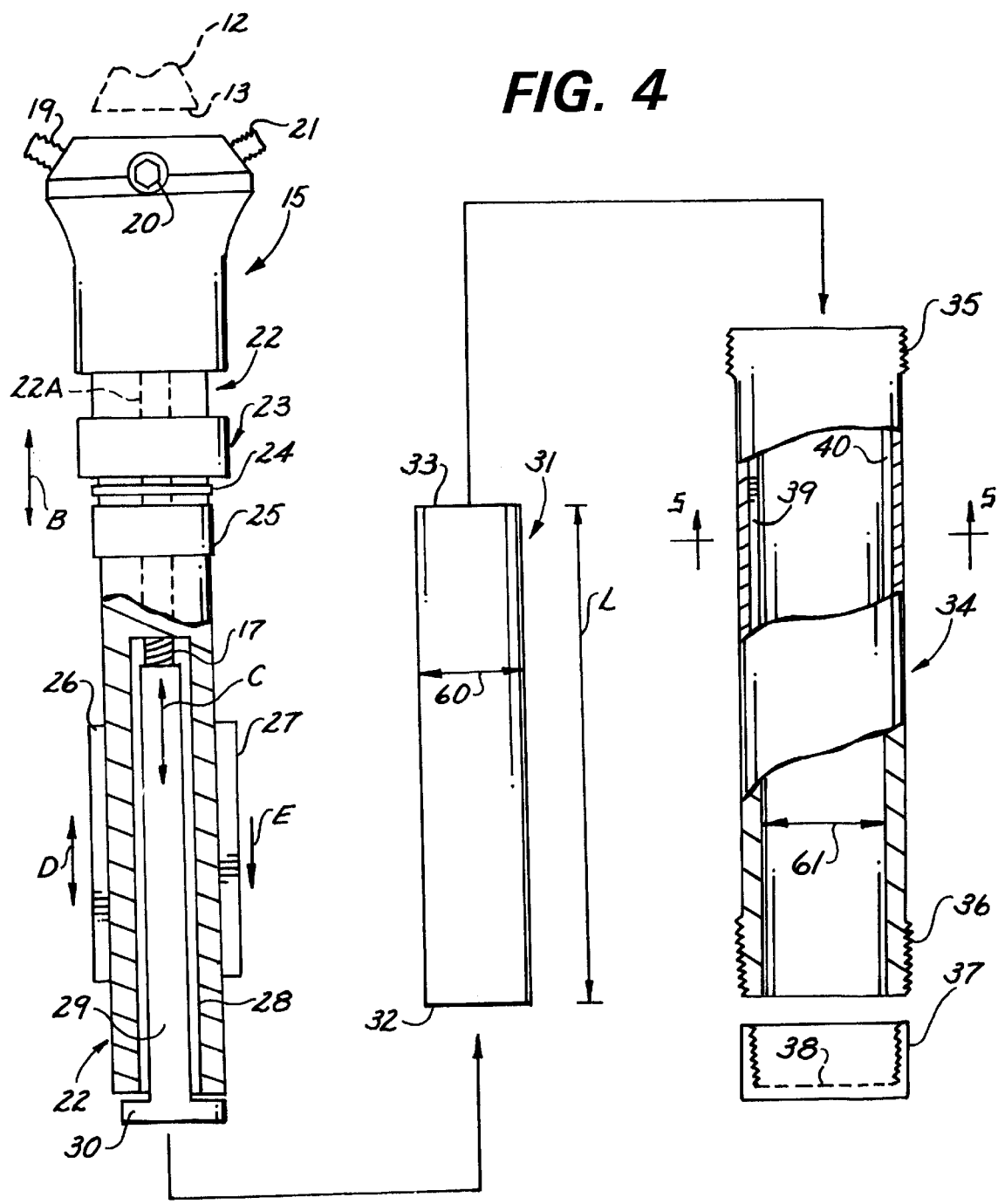
FIG. 4 is an assembly view of the compression-rebound unit utilized in the leg prosthesis of the invention.

FIG. 4 is an assembly view of the compression-rebound unit utilized in the leg prosthesis of the invention. Coupling member 15 is fixedly attached to cylindrical rod 22 such that the threaded end of set screw 17 extends through internally threaded aperture 22A in rod 22 and into cylindrical aperture 28. A plunger includes cylindrical leg 29 and circular head 30. Leg 29 is fixedly connected to head 30 and is slidably received by aperture 28. Screw 17 is turned into or out of aperture 22A to raise and lower in the directions indicated by arrows C the position of leg 29 in aperture 28. Opposed, parallel, elongate rectangular keys 26, 27 are seated on the outer cylindrical surface of rod 22. Keys 26, 27 are each slidably received by a slot 39, 40 formed in the inner cylindrical wall of hollow cylindrical housing 34. Keys 26, 27 can be impregnated with a lubricant to facilitate the sliding movement of the keys in slots 39, 40. The upper end 35 and lower end 36 of housing 34 are each externally threaded.

In FIG. 4, cap 23, rubber O-ring 24, and cylindrical hollow spacer 25 can slide up and down rod 22. When the compression-rebound unit of FIG. 4 is assembled in the manner shown in ghost outline in FIG. 6, cap 23 threads onto upper end 35 such that spacer 25 is inside housing 34 seated against the upper ends of keys 26, 27 in FIG. 4 and O-ring 24 is compressed between spacer 25 and the top 131 of cap 23. Further, cylindrical unitary elastomer unit 31 is positioned inside housing 34 such that one end 32 of unit 31 contacts the top 38 of cap 37 and the other end 33 of unit 31 contacts plunger head 30. When the compression-rebound unit of FIG. 4 is assembled, screw 17 is preferably adjusted such that unit 31 is slightly compressed between head 30 and the top 38 of cap 37.

FIG. 5 illustrates the positioning of keys 26 and 27 in slots 39 and 40 after the compression-rebound unit of FIG. 4 is assembled.

The diameter, indicated by arrows 60, of cylindrical elastomer unit 31 is presently less than the inner diameter, indicated by arrows 61, of hollow cylindrical housing 34 so that when unit 31 is compressed and shortened there preferably is space intermediate unit 31 and the inner wall of housing 34 into which unit 31 can laterally expand. This expansion space intermediate unit 31 and housing 34 is preferred because compression of unit 31 could be obstructed if the diameter of unit 31 closely approximated the inner diameter of housing 34. For example, when a solid cylindrical unit 31 is presently utilized, the outer diameter of the unit 31 is 0.69 inch while the inner diameter of housing 34 is 0.875 inch. Another way to provide expansion space for unit 31 would be to utilize a hollow unit 31.

The length, indicated by arrow L in FIG. 4, of unit 31 can vary as desired. One or more units 31 can be inserted in housing 34. If two or more units 31 are stacked on top of one another, or side by side, or otherwise inserted together in member each unit can have the same or different durometers, the same or different dimensions, etc. The length L of unit 31 presently is in the range of one inch to six inches for an adult and one-half to six inches for a youngster.

In use, after the compression-rebound unit of FIG. 4 is assembled in the manner shown in FIG. 6, head 13 of connection component 10 is inserted in opening 18 and is secured in opening 18 by turning each of set screws 19 to 22 against a side 12 of head 13. The lower end 36 and cap 37 threaded onto end 36 are slid into hollow cylindrical collar 39, after which screw 43 is turned into internally threaded apertures 44 and 45 to draw flanges 41 and 42 together to close and reduce the width of U-shaped slot 40 such that cap 37 is removably compressed in collar 39. Collar 39 is secured to artificial foot 46. Connection component 10 is mounted in the direction of arrow A on the distal end of the remaining length or portion of the leg of a handicapped individual who is standing. Prior to mounting component 10 on the leg portion of a standing individual, component 10 is rotated from the orientation illustrated in FIG. 1B counterclockwise about an axis perpendicular to the plane of the sheet of paper of the drawings through an arc of ninety degrees such that arrow A is vertically oriented instead of being horizontal oriented as shown in FIG. 1B. (If component 10 is mounted in the direction of arrow A in FIG. 1B onto the horizontally oriented leg portion of a sitting individual, then the orientation of component 10 in FIG. 1B need not be changed.) Further, after component 10 is so rotated counterclockwise from the orientation shown in FIG. 1B through a ninety degree arc, plate 11 is horizontal instead of being vertically oriented in the manner shown in FIG. 1B.

Once component 10 is mounted on a portion of the leg of an individual, the individual can walk on the prosthetic leg of the invention. When the individual puts his weight on the leg prosthesis, a downward force is generated against component 10 and coupling 15. The force acts in the direction of arrow F, causes head 30 to compress elastomer unit 31, and cause rectangular keys 26 and 27 to slide downwardly in the direction of arrow E in slots 39 and 40. Head 30, shaft 29, and rod 22 move in the direction of arrow E simultaneously with keys 26 and 27. When elastomer unit 31 is compressed, the length L of unit 31 is shortened and unit 31 expands laterally toward and against the inner cylindrical surface of housing 34. Unit 31 is compressed an amount sufficient to absorb the downward force acting in the direction of arrow F. When the individual's weight begins to shift to his other leg while the individual continues to walk, the force generated in the direction of arrow F against component 10 and elastomer unit 31 begins to decrease. As the force acting against unit 31 gradually decreases, unit 31 expands in the direction of arrow D and increases in length, and rod 22 and coupling 15 move simultaneously in the direction of arrows D and G, respectively. When rod 22 moves in the direction of arrow D, keys 26 and 27 simultaneously slide upwardly through slots 39 and 40 in the direction of arrow D. Since keys 26 and 27 are fixedly attached to rod 22, rod 22 and keys 26 and 27 move simultaneously with respect to housing 34. Unit 31 expands to its original uncompressed length L or expands to within 5%, preferably 2%, of its original incompressed length L.

Unit 31 preferably has a durometer in the range of 45 to 80.

Elastomer unit 31 is presently preferably comprised of microcellular polyurethane, although the elastomer can be constructed from any other desired materials. The polyurethane preferably rebounds (expands to its original uncompressed length) at a linear rate which is slower than the linear rate at which the polyurethane is compressed. For example, a unit 31 consisting of one polyurethane composition was 0.69 inches in diameter, six inches long, and had a durometer of 70. Testing of the unit produced the data noted below in Table I.

TABLE I

| Linear Compression (mm) | Force Applied During Compression (lbs/in2) (FC) ** | Force Generated By Unit 31 During Expansion (lbs/in2) (FR) ** | FC/FR |
|---|---|---|---|
| 2 | 34.75 | 5.35 | 6.50 |
| 4 | 61.50 | 26.74 | 2.30 |
| 6 | 80.21 | 45.45 | 1.76 |
| 10 | 112.30 | 74.87 | 1.50 |
| 14 | 147.06 | 104.28 | 1.41 |
| 20 | 208.56 | 157.75 | 1.32 |
| 24 | 243.31 | 203.21 | 1.20 |
| 30 | 310.16 | 275.40 | 1.13 |
| 34 | 366.10 | 334.22 | 1.10 |

** No time delay between full compression (34 mm compression) and beginning of rebound (expansion). The data in Table I are average values obtained from the continuous repeated cyclic compression and release of a polyurethane unit 31 over a thirty minute period. Each compression--release cycle took about four seconds. During the first part of each cycle, the time elapsed from beginning of force application to full compression (34 mm) was two seconds. During the last part of each cycle, the time elapsed from the beginning of the release of the compressive force to the complete release of compressive force and elastic expansion of elastomer back to nearly its entire original length was two seconds.

Since the force required to compress the unit 31 to a certain length was, as noted by the FC/FR ratio in TABLE I, greater than the force required to maintain unit 31 at that certain length during expansion of the unit 31, unit 31 expanded and recovered its original shape more slowly than it was compressed. The FC/FR ratio was not one or nearly one but was greater than 1, typically at least about 1.10 for compressive forces in the range of fifty to about 300 pounds per square inch. An elastomer which, when a cylindrical unit 31 of the elastomer is tested which has a diameter of 0.69 and length of six inches, has an FC/FR ratio in excess of 1.10 for compressive and rebound forces in the range of fifty to three hundred pounds per square inch is preferred in the practice of the invention and makes the leg prosthesis of the invention unusually comfortable. An FC/FR ratio equal to one is not acceptable in the practice of the invention because this simulates a spring which expands as rapidly as it compresses. When an elastomer linearly expands at a rate which is as rapid as the rate at which it is linearly compressed, the comfort afforded by the apparatus of the invention is adversely impacted.

The FC/FR ratio cannot be too great, otherwise, the elastomer unit 31 will not rebound quickly enough or will not substantially return to its original length when it rebounds. Consequently, when an elastomer unit 31 which is 0.69 inches in diameter, is six inches long, and is subjected to a force of three hundred pounds and is allowed to rebound, the average FC/FR for compression (FC) and rebound (FR) forces in the range of fifty to 300 pounds per square inch is in the range of 1.10 to 3.00, preferably 1.10 to 2.00. The average FC/FR for the material tested in Table I above for compressive and rebound forces of fifty to 300 pounds per square inch is in the range of 1.10 to 2.00. The average FC/FR value is obtained by averaging the FC/FR values for at least ten equally spaced linear compression values between fifty and three hundred pounds of compression (FC) and rebound (FR) forces. Table I does not includes ten FC/FR values for equally spaced linear compression values for compression (FC) and rebound (FR) forces between 50 and 300 hundred pounds. It is, however, obvious that ten such averaged values would have a value between 1.10 and 2.00.

Unit 31 is presently preferably cylindrical but be square or any other desired shape and dimension. Unit 31 can be hollow or perforated.

When unit 31 is compressed in the direction of arrow E when an individual walks on the leg prosthesis of the invention, the length L of unit 31 is reduced (compressed) by an amount in the range of one-quarter of an inch to three inches, preferably one-quarter of an inch to one inch, when a force in the range of 200 pounds per square inch to 1000 pounds per square inch is applied to the upper circular end 33 of unit 31. End 33 has an area equal to the cross-sectional area of unit 31. The cross-sectional area of unit 31 is perpendicular to axis 31C in FIG. 4, and is circular. If unit 31 is compressed by less than one-quarter of an inch or more than about three inches, use of the leg prosthesis of the invention can be awkward and uncomfortable. In addition, when unit 31 is compressed in the direction of arrow E when an individual walks on the leg prosthesis of the invention and applies a force in the range of 200 pounds per square inch to 1000 pounds per square inch to the upper circular end 33 of unit 31, the length L of unit 31 is preferably reduced by twenty to forty percent of its original non-compressed length L. By way of example, a force of thirteen pounds applied to the entire area of a circular end 33 of a unit 31 which has a diameter of 0.69 inches and a cross-sectional area of 0.374 square inches generates a force equal to 34.75 pounds per square inch; a force of two pounds applied to the same circular end 33 (the area of which is 0.374 square inches) of unit 31 produces a force equal to 5.35 pounds per square inch; and, a force of 23.00 pounds applied to end 33 of unit 31 produces a force equal to 61.50 pounds per square inch.

It is also preferred that the unit 31 be comprised of polyurethane or of another elastomer which is compressed an amount equal to twenty to forty percent of its original uncompressed length when a compressive force in the range of 200 to 1000 pounds per square inch is applied to a unit which has a diameter of 0.69 inch and a length of six inches. The compressive force acts in a direction parallel to the centerline 31C of unit 31. When unit 31 is in its original uncompressed undeformed state, each point on the cylindrical outer surface of unit 31 is equidistant from centerline 31C.

Figure 7:
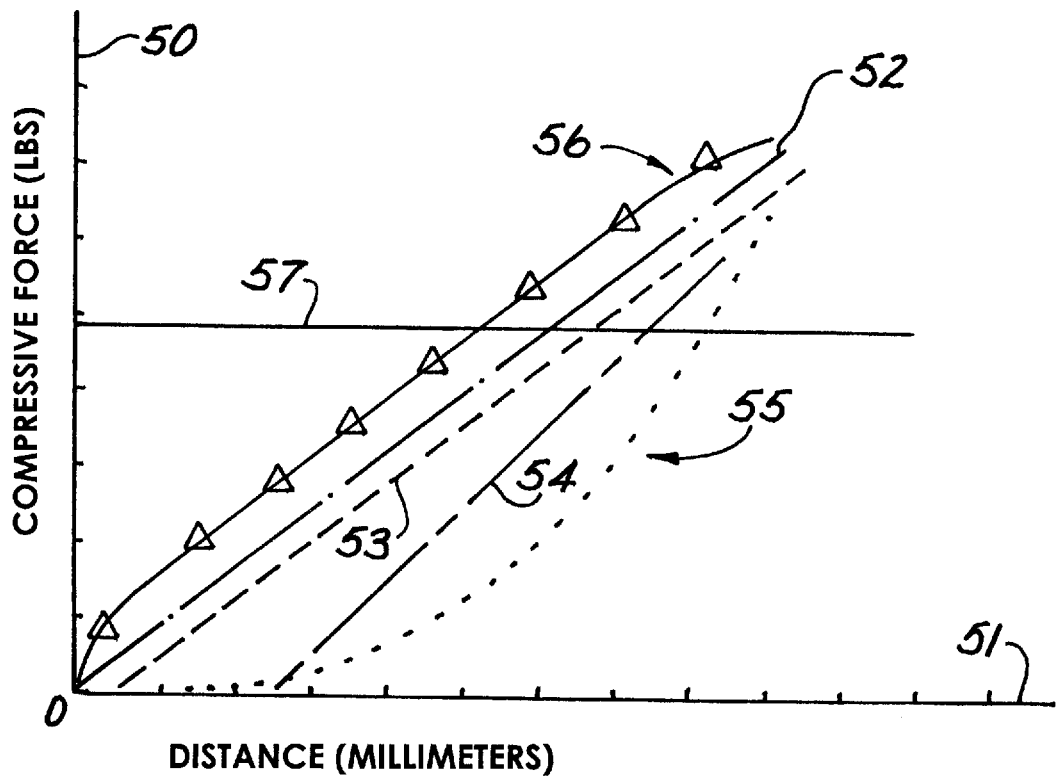
FIG. 7 is a graph illustrating the compression and rebound characteristics of the elastomer utilized in the practice of the invention.

The elastic compression and expansion properties of one elastomer unit 31 utilized in the practice of the invention are illustrated in FIG. 7. Dash-dot line 52 illustrates the compression of a unit 31 while dashed line 53 illustrates the expansion of unit 31 in reaction to the applied compressive force indicated on the horizontal axis 50. The amount in millimeters by which unit 31 is shortened from its original non-compressed length is indicated on axis 51. As can be seen from line 57, when a compressive force equivalent to that intersected on axis 50 by line 57 is applied to a unit 31, the linear compression of unit 31 for a given compressive force is less than the linear compression of unit 31 when unit 31 generates the equivalent force during the expansion or rebound of unit 31. In the practice of the invention, the rebound of unit 31 would not be represented by line 56 in FIG. 7 because line 56 indicates that the rate of linear expansion of unit 31 is faster than the rate of linear compression of unit 31. The rebound of a unit 31 utilized in the practice of the invention also would preferably not be represented by line 54 in FIG. 7 because line 54 indicates that unit 31 does not return to its original length. It is possible that a unit 31 utilized in the practice of the invention could have a rebound corresponding to line 55 because line 55 indicates that unit 31 returns to its original length. It is also possible, however, that a unit 31 with a line 55 type rebound would not be acceptable in the invention because it would take the unit too long to return to its original length.

If in FIG. 7 line 52 represented both the rate of linear compression of a unit 31 and the rate of linear expansion of unit 31 after the compressive force acting on unit 31 was released, then the rate of linear expansion of unit 31 would equal the rate of linear compression of unit 31. When the rates of linear expansion and linear compression of unit 31 are identical, unit 31 returns to its original shape just as quickly as it was compressed. This is not desirable in the practice of the invention.

As used herein, the term rate of linear compression indicates how quickly a unit is linearly compressed by a force FC from its original length (compressed or uncompressed) to a resulting shorter length. The term rate of linear expansion indicates how quickly a unit 31 linearly expands from its resulting shorter length to its original length once the compressive force FC is released. If a compressive force FC compresses a unit 31 two inches in one second, but unit 31 takes 1.5 seconds to return to its original length after the compressive force FC is released, then the rate of linear compression is faster than the rate of linear expansion.

Figure 8:
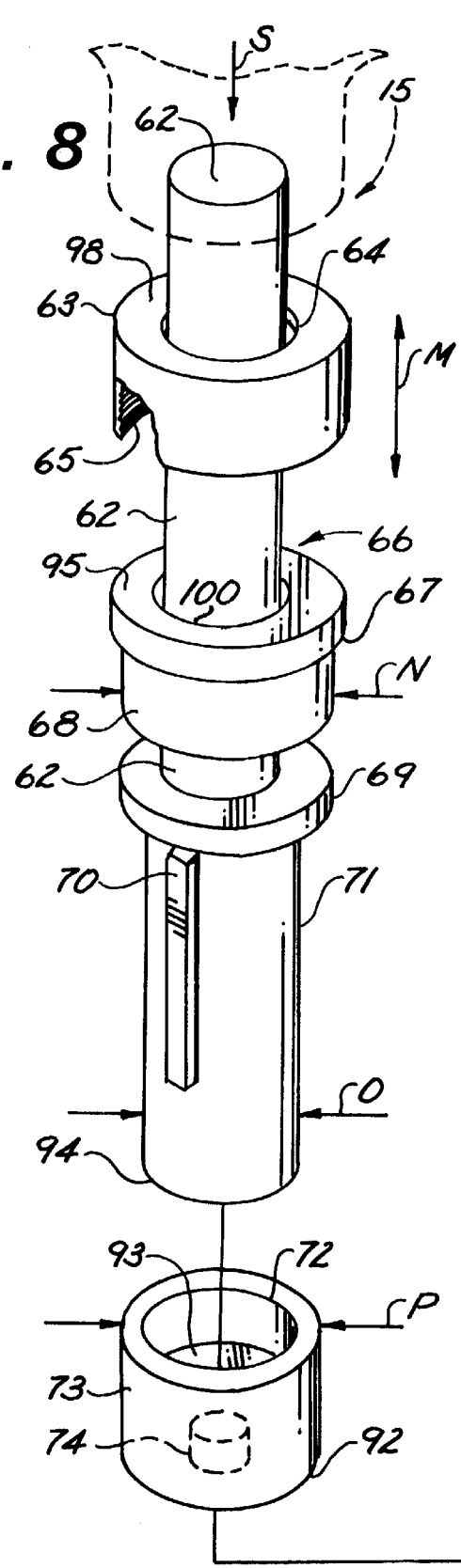
FIG. 8 is an exploded assembly view of another embodiment of the invention.
Figure 8:
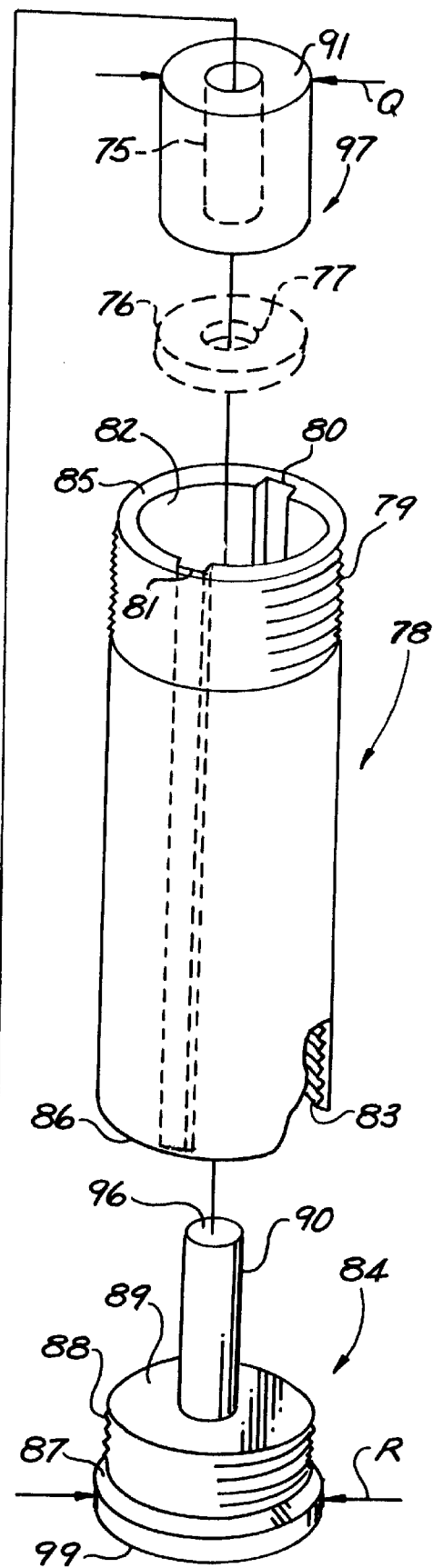

In one embodiment of the invention, a user is supplied with a kit including a plurality of separate units 31 each having a different length and/or durometer. The user puts units 31 of differing length and/or durometer, or puts stacked combinations of units 31 of differing length and/or durometer, into the prosthetic leg of the invention and tests how the prosthetic leg functions and feels when the user walks on the prosthetic leg. The user selects the unit 31 or combination of units 31 which is most comfortable to the user. An alternate embodiment of the invention is illustrated in FIG. 8 and includes cylindrical metal rod 62. A coupling member, indicated in FIG. 8 by dashed lines 15, is affixed to the upper end of rod 62. Hollow cylindrical cap 63 includes aperture 64 sized to permit cap 63 to slide along rod 62 in the directions indicated by arrows M. Cap 63 is internally threaded 65. Cylindrical member 66 circumscribes rod 62 and includes upper surface 95 and bottom surface 67. Surface 95 circumscribes rod 62. Surface 95 bears against the circular undersurface of the top 98 of cap 63 when the apparatus of FIG. 8 is assembled. Cylindrical member 68 circumscribes rod 62 and is centered on and fixedly secured to member 66. Cylindrical aperture 100 is formed through members 66 and 68. Rod 62 slides through aperture 100. The outer diameter, indicated by arrows N, of member 68 is less than the outer diameter of member 66 such that surface 67 circumscribes the upper end of member 68. The outer diameter of bottom surface 67 equals the outer diameter of flat circular upper surface 95. When the apparatus of FIG. 8 is assembled, surface 67 rests on and bears against the circular lip surface 85 of housing 78. The outer diameter N of member 68 is less than the inner diameter of housing 78 such that member 68 can be slidably inserted inside housing 78.

Cylindrical member 69 is fixedly secured to rod 62, as is cylindrical member 71. A pair of opposed upstanding elongate keys 70 are fixedly secured to the outer surface of cylindrical member 71. The outer diameter of member 69 is slightly less than the diameter of inner cylindrical surface 82 so that member 69 can slide inside housing 78. When the apparatus of FIG. 8 is assembled, each key 70 is slidably received by a different one of elongate slots 80 and 81 formed in the inner cylindrical wall or surface 82 of hollow cylindrical housing 78. The outer diameter, indicated by arrows O, of member 71 is slightly less than the diameter of cylindrical opening 72 formed in cap 73 such that cap 73 can be press fit on the lower end of member 71. The lower flat circular end 94 of member 71 seats on and contacts the flat circular floor 93 of cap 73. Cylindrical opening or detent 74 is formed in the circular surface 92 of cap 73. Detent 74 is spaced apart from floor 93. Detent 74 is shaped to slidably receive, if necessary, the upper end 96 of cylindrical pin 90 when unit 97 is compressed during operation of the apparatus of FIG. 8. The outer diameter, indicated by arrows P, of cap 73 is slightly less than the diameter of inner cylindrical surface 82 so that cap 73 can slide along surface 82 of housing 78.

Cylindrical elastomer unit 97 includes cylindrical aperture 75 centered on the longitudinal centerline of unit 97. Aperture 75 slidably receives pin 90. Pin 90 presently preferably extends only partially through aperture 75. Upper circular surface 91 bears against surface 92 of cap 73 when the apparatus of FIG. 8 is assembled.

If desired, a washer 76 can be interposed between unit 97 and circular surface 89 of fitting 84 to partially pre-compress unit 97. Pin 90 slidably extends through aperture 77 in washer 76. If washer 76 is not utilized, then the bottom circular end of unit 97 contacts surface 89 when the apparatus of FIG. 8 is assembled. The outer diameter, indicated by arrows Q, of unit 97 is less than the diameter of the inner cylindrical surface 82 of housing 78. Diameter Q is less than the diameter of surface 82 by an amount which permits the outer cylindrical surface of unit 97 to be spaced apart from surface 82 such that the outer cylindrical surface of unit 97 can freely expand laterally when unit 97 is compressed during use of the apparatus of FIG. 8. If the diameter Q is very close to the diameter of surface 82, then unit 97 can not readily compress because space is not be available between unit 97 and surface 82 to permit the lateral expansion of unit 97. Unit 97 has a shape and dimension and properties equivalent to those described earlier for unit 31.

The upper end 79 of hollow cylindrical housing 78 is externally threaded. When the apparatus of FIG. 8 is assembled, threads 65 of cap 63 turn onto the threads on end 79 and cap 73 secures member 66 against lip surface 85. The lower end of housing 78 is internally threaded 83. When the apparatus of FIG. 8 is assembled, the external threads 88 on fitting 84 turn into threads 83 and circular surface 87 of cap 99 of fitting 84 bears against circular lip 86 on the bottom of housing 83. The outer diameter, indicated by arrows R, of cap 99 is identical to that of housing 78 and member 66. Pin 90 functions to keep unit 97 in a desired position in housing 78 prior to and during compression of unit 97. Unit 97 is preferably presently (but not necessarily) centered in housing 78 and spaced apart from surface 82.

When the apparatus of FIG. 8 is assembled, member 68, member 69, member 71, cap 73, unit 97, washer 76 (if utilized), pin 90, and threads 88 are each inside housing 78. Cap 73 slidably contacts the inside surface 82. Under surface 67 bears against circular lip 85. Surface 87 bears against circular lip 86. Pin 90 slidably extends through aperture 77 and partially into aperture 75. The apparatus of FIG. 7 can be utilized intermediate the artificial foot 46 of FIG. 6 and the connection component 10 of FIGS. 1A and 1B in place of the apparatus of FIGS. 2 to 5. When the apparatus of FIG. 8 is utilized instead of the apparatus of FIGS. 2 to 5, the lower end of housing 78 (including cylindrical cap 99 of fitting 84) is secured in collar 39, while the coupling (indicated by dashed line 15 in FIG. 8) is connected to component 10. After the apparatus of FIG. 7 is so installed and the user walks on the apparatus, a downward force is generated on the apparatus in the direction of arrow S in FIG. 8. The downward force S causes keys 70 to slide downwardly along slots 80 and 81 in the direction of arrow S. When keys 70 slide, rod 62 and members 69, 71, and 73 are simultaneously displaced with keys 70 in the direction of arrow S, compressing unit 97. Rod 62 slides through aperture 100 in members 66 and 68 and through aperture 64 in cap 63. When rod 62 (along with members 69, 71, and 73 and keys 70) slides in housing 83, cap 63, members 66 and 68, washer 76, and fitting 84 are fixed, in much the manner that the cylindrical housing of a shock absorber is fixed while the plunger or piston of the shock absorber moves in the housing. In order for members 69, 71 and 73 to slide in the direction of arrow S in housing 78, unit 97 must elastically compress. When unit 97 elastically compresses it slides down pin 90 and expands laterally outwardly toward inner surface 82. If unit 97 is compressed a sufficient amount, then the upper end 96 of pin 90 may slide into detent 74. When the force S is released (when the user picks his leg and the apparatus of FIG. 8 up off the ground), rod 62 (along with members 69, 91, and 73 and keys 70) slide in housing in a direction opposite that of arrow S, allowing unit 97 to elastically expand back to its normal shape and dimension.

Keys 26 and 27 and/or housing 34 (and, consequently, the sides and bottom of slots 39, 40), keys 70 and/or housing 78 (and, consequently, the sides and bottom of slots 80, 81), spacer 25, members 66 and 68, and/or cap 73 each can be fabricated from a self lubricating polymer bearing material. By way of example, and not limitation, polymer material for keys 26, 27, and/or 70 can be obtained from the Polymer Corporation of 2120 Fairmont Avenue Post Office Box 14235 Reading, Pa. 19612-4235. Telephone: 800 729 0101. FAX: 800 366 0301. One self lubricating polymer bearing material which can be obtained from the Polymer Corporation is polyetherkeytone (PEEK), called POLYPENCO (™). POLYPENCO is semicrystalline and is an extruded nylon compound. A second self lubricating polymer bearing material which can be obtained from the Polymer Corporation is NYLATRON (™). NYLATRON is a self-lubricating nylon bearing material which can be injection molded, extruded, or machined. Keys 26, 27, and/or 70 are presently produced by injection molding the key and then finish machining the keys to desired tolerances. A third self lubricating polymer bearing acetal material which can be obtained from the Polymer Corporation is ACETRON (™). A fourth self lubricating polymer bearing material which can be obtained from the Polymer Corporation is UHMW (™) ultra high molecular weight nylon. POLYPENCO, NYLATRON, ACETRON, and UHMW can be filled with glass, carbon, teflon or other desired lubricating materials.

The coefficient of friction of POLYPENCO is about 0.4; of NYLATRON is about 0.16; of ACETRON is about 0.20; and, of UHMW is about 0.10. The coefficient of friction of the polymer bearing material utilized to make keys 26, 27, 70, cap 73, etc. is in the range of 0.05 to 0.60, preferably 0.10 to 0.40.

The coefficient of linear thermal expansion of NYLATRON is $3.5 \times 10$ to the fifth power in./in./F; of ACETRON is $4.7 \times 10$ to the fifth power in./in./F; of POLYPENCO is $2.6 \times 10$ to the fifth power in./in./F; and, of UHMW is $1.2 \times 10$ to the fifth power in./in./F. The coefficient of linear thermal expansion of the polymer bearing material is in the range of $1.0 \times 10$ to the fifth power to $6.0 \times 10$ to the fifth power, preferably $1.0 \times 10$ to the fifth power to 5.0 and 10 to the fifth power in./in./F.

The tensile strength of NYLATRON is 10,500 psi at 73 degrees F; of POLYPENCO is 16,000 psi at 73 degrees F.;

of ACETRON is 7,500 psi at 73 degrees F; and of UHMW is 12,400 psi at 73 degrees F. The tensile strength of the polymer bearing material is in the range of 1,100 psi to 20,000 psi at 73 degrees F, preferably 5,000 psi to 20,000 psi at 73 degrees F.

The shear strength of the polymer bearing material is also important because a high shear strength material resists deflection and change in the shape and contour of a surface. The shear strength of NYLATRON is 9,000 psi at 73 degrees F; of POLYPENCO is 8,000 psi at 73 degrees F; of ACETRON is 6,000 psi at 73 degrees F; and of UHMW is 15,000 psi at 73 degrees F. The shear strength of the polymer bearing material is in the range of 2,000 to 20,000 psi at 73 degrees F, preferably 4,000 to 20,000 psi at 73 degrees.

The coefficient of friction, coefficient of linear thermal expansion, tensile strength, and shear strength of the self lubricating polymer bearing material are critical, particularly in connection with movement of keys 26, 27, 70. Keys 26, 27, 70 must not distort or deform under tensile forces, under shear forces, and under high temperatures and must readily slide along the grooves in which the keys are seated. While keys 26, 27, 70 and the grooves in which the keys ride can be fabricated from any desired material, a self lubricating polymer bearing material is presently preferred.

Another source of self lubricating polymer bearing materials is the Pacific Bearing Company of PO Box 6980, Rockford, Ill., 61125-6980, 800 962 8979, FAX 815 962 3818. One polymer bearing material sold by the Pacific Bearing Company is RULON (™). RULON is 85% glass and 14% TEFLON (™) and has a coefficient of friction of 0.15.

One or more ball bearings made of a self lubricating polymer bearing material can be utilized in place of a key 26, 27, 70 and can roll or slide along a groove 39, 80, 81.

Housings 78 and 34 can be fabricated from a metal and/or a polymer.

Units 31 and 97 can be provided in different lengths, diameters, shapes, and/or durometers. A plurality of shorter elastomer units can be stacked to a height about equivalent to a single unit 31 or 97 (or any other desired height) and utilized in place of a unit 31 or 97. Each elastomer unit in a "stack" of units utilized instead of a single unit 31 or 97 can have a different durometer or have other physical properties which vary from elastomer unit to elastomer unit. For example, polyurethane has a quicker rate of return to its original length than does MCU or microcellular urethane. But MCU can be "softer" than polyurethane and can initially compress more readily than polyurethane. Consequently, combining in a single "stack" of elastomers elastomer units having different rates of return to their original length (for an elastomer unit of a shape and dimension) can be advantageous. One source of MCU (microcellular urethane) is Freudenbergnok of 50 Amon Drive, Manchester N.H. 03103-3388. Telephone: 603 669 4050. FAX: 603 627 3718. Polyurethane elastomer rods of differing durometer and diameter are marketed by Kryptonics of 740 South Pierce Ave, Lewisville, Colo. Telephone: 303 665 5353. FAX: 303 655 1318.

Figure 9:
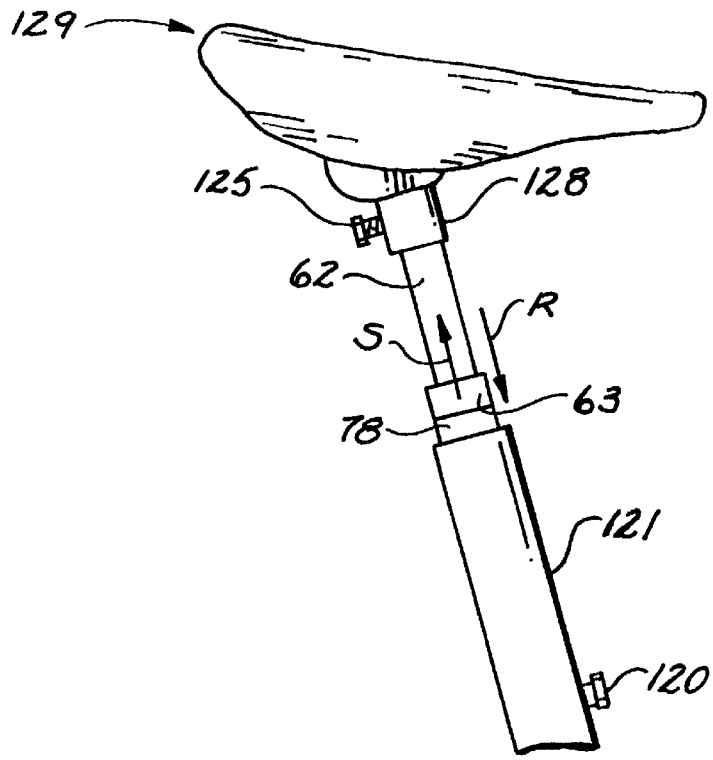
FIG. 9 is a side view illustrating the compression-rebound unit of FIG. 8 installed as a seat post in a bicycle; and, FIG. 10 is a side view illustrating the compression-rebound unit of FIG. 8 installed a shock absorber at the steering head-fork junction of a bicycle.

The compression-rebound unit described in FIG. 8 (or the unit described in FIGS. 4 and 5) can be utilized in a bicycle to absorb impacts resulting when the bicycle travels over bumps or objects on the ground. In FIG. 9, the upper end of rod 62 of the compression-rebound unit of FIG. 8 is secured in an attachment assembly 128 by a set screw 125. In this embodiment of the invention, coupling member 15 is not utilized and is removed from the upper end of rod 62 and set aside. The assembly 128 is attached to bicycle seat 129. The housing 78 of the compression-rebound unit of FIG. 8 is slidably inserted in the hollow cylindrical bicycle seat post mast 121 and is secured in the mast with a set screw 120. The compression-rebound unit operates in the manner described earlier. When the bicycle traverses a bump, rod 62 and seat 129 move downwardly in the direction of arrow R. Rod 62 slides into housing 78 to compress unit 97. Unit 97 then rebounds and displaces rod 62 and seat 129 in the direction of arrow S when unit 97 elastically expands to its original shape and dimension.

Figure 10:
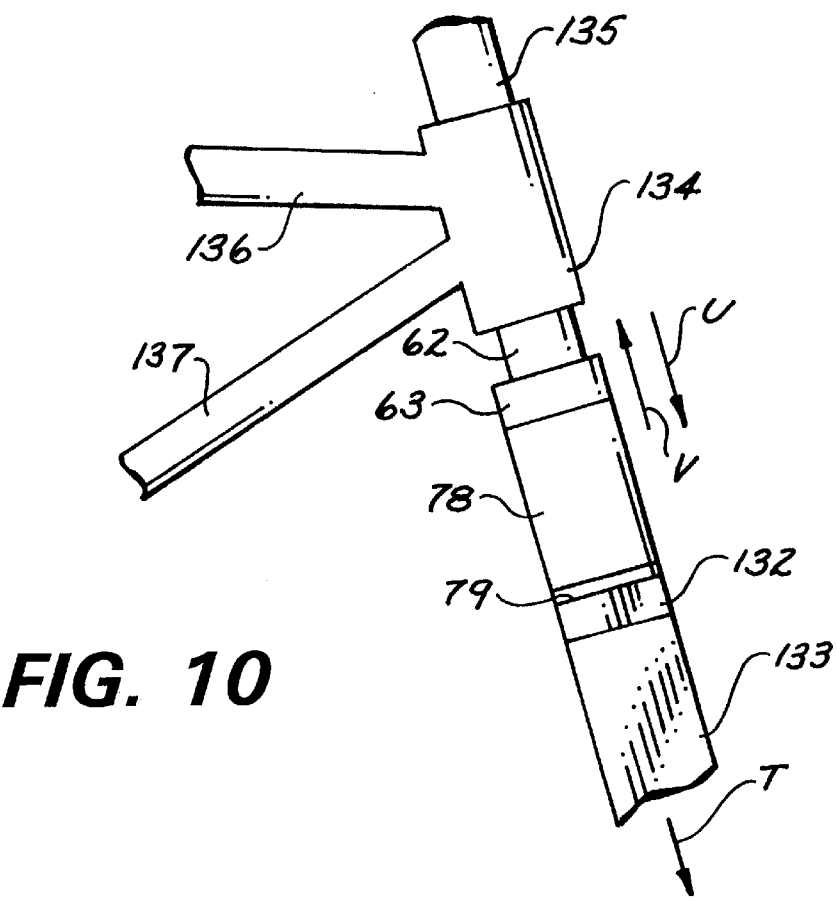

In FIG. 10, the upper end of rod 62 of the compression-rebound unit described in FIG. 8 (or the unit shown in FIGS. 4 and 5) is fixedly secured in the hollow cylindrical steering head 134 of a bicycle. The upper end of rod 62 is secured in head 134 with a set screw, by welding, or by any other desired means. In the embodiment of the invention in FIG. 10, member 15 is not utilized and is removed from rod 62 and set aside. The bottom 99 of the compression-rebound unit is connected to the top member 132 of the bicycle fork assembly. Fork 133 is attached to member 132. Fork 133 extends down in conventional fashion in the direction of arrow T toward the center of the front wheel of a bicycle. Top tube 136 and down tube 137 are connected to steering head 134. The handle bar unit 135 is connected to the steering head 134. The compression-rebound unit of FIG. 10 operates in the manner described earlier. When the bicycle traverses a bump, steering head 134 and rod 62 move downwardly in the direction of arrow U. Rod 62 slides into housing 78 to compress elastomer unit 97. Unit 97 then rebounds and displaces rod 62 and head 134 in the direction of arrow V when unit 97 elastically expands to its original shape and dimension.

As would be appreciated by those of skill of the art, the compression-rebound unit of FIG. 8 can be utilized in the stock of a shotgun to absorb recoil forces generated when the fun is fired.

Having described my invention in such terms as to enable those skilled in the art to understand and practice it, and having described the presently preferred embodiments thereof,

I claim:

1. A prosthetic apparatus adapted for emplacement on the distal end of a leg member, comprising:
    (a) connection means adapted to be mounted on the distal end of a leg member;
    (b) foot means for contacting the ground; and,
    (c) a compression-rebound unit interconnecting said connection means and said foot means and including:
        (i) a housing;
        (ii) a resilient elastomer mounted in said housing for compression and post-compression expansion;
        (iii) a displacement member extending into said housing, said member moving in a first direction of travel and compressing said resilient elastomer when a first force is exerted against said member to press said member against said elastomer and compress said elastomer, and moving in a second direction of travel opposite said first direction of travel when said first force is released and permits said elastomer to rebound and elastically expand;
        (iv) key means for sliding said displacement member in said housing along a linear axis of travel, said key means including at least one self-lubricated elongate member extending parallel to said linear axis of travel and to said first direction of travel, and slot means slidably receiving said elongate member.

2. A method for emplacing a prosthesis on the distal end of a leg member, comprising the steps of:
(a) providing a prosthetic apparatus including:
  (i) connection means adapted to be mounted on the distal end of a leg member;
  (ii) foot means for contacting the ground; and,
  (iii) a compression-rebound unit interconnecting said connection means and said foot means and including:
    a housing,
    a plurality of resilient elastomer units each adapted to be mounted adjacent said housing for compression and post-compression expansion, each of said elastomer units having a different linear compressibility for a given compressive force;
    a displacement member extending into said housing, said member moving in a first direction of travel and compressing said resilient elastomer when a first force is exerted against said member to press said member against said elastomer and compress said elastomer, and moving in a second direction of travel opposite said first direction of travel when said first force is released and permits said elastomer to rebound and elastically expand;
(b) mounting one of said elastomer units adjacent said housing;
(c) mounting said prosthetic apparatus on the distal end of a leg member of a user;
(d) walking on said leg member to test the comfort of said prosthetic apparatus to the user;
(e) repeating steps (b) to (d) for each of the remaining ones of said elastomer units; and,
(f) selecting one of said elastomer units for use in said prosthetic apparatus.

3. A bicycle including:
(a) a frame; and,
(b) a compression-rebound unit mounted in said frame and including:
  (i) a housing;
  (ii) a resilient polyurethane elastomer mounted in said housing for compression and post-compression expansion, said elastomer having an original length and having an FC/FR ratio in the range of 1.10 to 3.00 for compression and rebound forces in the range of fifty to three hundred pounds per square inch;
  (iii) a displacement member extending into said housing, said member moving in a first direction of travel and compressing said resilient elastomer when a first force is exerted against said member to press said member against said elastomer and compress said elastomer to a length less than said original length, and moving in a second direction of travel opposite said first direction of travel when said first force is released and permits said elastomer to rebound and elastically expand;
  (iv) key means for sliding said displacement member in said housing along a linear axis of travel, said key means including at least one self-lubricated elongate member extending parallel to said linear axis of travel and to said first direction of travel, and slot means slidably receiving said elongate member;
the rate of linear expansion of said elastomer after a compressive force is applied to said elastomer and released being slower than the rate of linear compression of said elastomer during the application of said compressive force.

4. The apparatus of claim 3 wherein said elastomer on rebounding expands to within two percent of said original length.

* * * * *